(12) United States Patent
Egorov et al.

(10) Patent No.: US 7,510,691 B2
(45) Date of Patent: Mar. 31, 2009

(54) METHOD FOR IMPROVING THE RECOVERY OF CESIUM-131 FROM BARIUM CARBONATE

(75) Inventors: Oleg Egorov, West Richland, WA (US); Sergey Zlokazov, Zarechnyi (RU); Arsen Dzhanelidze, Zarechnyi (RU); Sergey Tretyakov, Zarechnyi (RU); David J. Swanberg, Kennewick, WA (US)

(73) Assignee: IsoRay Medical, Inc., Richland, WA (US)

( * ) Notice: Subject to any disclaimer, the term of this patent is extended or adjusted under 35 U.S.C. 154(b) by 142 days.

(21) Appl. No.: 11/712,205

(22) Filed: Feb. 27, 2007

(65) Prior Publication Data

US 2007/0212285 A1 Sep. 13, 2007

Related U.S. Application Data

(60) Provisional application No. 60/777,488, filed on Feb. 28, 2006.

(51) Int. Cl.
C01D 17/00 (2006.01)
(52) U.S. Cl. .......................................... 423/2; 423/249
(58) Field of Classification Search ...................... 423/2, 423/249
See application file for complete search history.

(56) References Cited

U.S. PATENT DOCUMENTS

| | | |
|---|---|---|
| 1,753,287 A | 4/1930 | Failla |
| 3,351,049 A | 11/1967 | Lawrence .................... 128/1.2 |
| 3,706,689 A | 12/1972 | Haskins ................ 252/301.1 R |
| 4,323,055 A | 4/1982 | Kubiatowicz ................ 128/1.2 |
| 4,702,228 A | 10/1987 | Russell, Jr. et al. ........... 128/1.2 |
| 4,784,116 A | 11/1988 | Russell, Jr. et al. ........... 128/1.2 |
| 4,891,165 A | 1/1990 | Suthanthiran ................ 252/633 |
| 4,994,013 A | 2/1991 | Suthanthiran et al. .......... 600/8 |
| 5,071,610 A | 12/1991 | Hagan et al. ................. 264/120 |
| 5,163,896 A | 11/1992 | Suthanthiran et al. .......... 600/8 |
| 5,342,283 A | 8/1994 | Good ............................. 600/8 |
| 5,368,736 A | 11/1994 | Horwitz et al. ............. 210/635 |
| 5,405,309 A | 4/1995 | Carden, Jr. ..................... 600/3 |
| 5,512,256 A | 4/1996 | Bray et al. ...................... 423/2 |
| 5,591,420 A | 1/1997 | Balmer ....................... 423/700 |
| 5,683,345 A | 11/1997 | Waksman et al. ............... 600/3 |
| 5,749,042 A | 5/1998 | Bray et al. ...................... 423/2 |
| 5,899,882 A | 5/1999 | Waksman et al. ............. 604/96 |
| 6,060,036 A | 5/2000 | Armini ...................... 424/1.29 |
| 6,066,302 A | 5/2000 | Bray ............................. 423/2 |
| 6,099,457 A | 8/2000 | Good ............................. 600/8 |
| 6,099,458 A | 8/2000 | Robertson ..................... 600/8 |
| 6,139,749 A | 10/2000 | Goken et al. ................ 210/651 |
| 6,306,074 B1 | 10/2001 | Waksman et al. ............... 600/7 |
| 6,309,614 B1 | 10/2001 | Horwitz et al. ................. 423/2 |
| 6,351,049 B1 | 2/2002 | Chassoulier et al. ........ 310/90.5 |
| 6,403,916 B1 | 6/2002 | Spooner et al. ........ 219/121.63 |
| 6,458,070 B1 | 10/2002 | Waksman et al. ............... 600/3 |
| 6,471,632 B1 | 10/2002 | Jahrmarkt et al. ............... 600/8 |
| 6,479,920 B1 | 11/2002 | Lal et al. ..................... 310/309 |
| 6,485,406 B1 | 11/2002 | Ziegler et al. .................. 600/8 |
| 6,503,185 B1 | 1/2003 | Waksman et al. ............... 600/3 |
| 6,554,756 B1 | 4/2003 | Schaart .......................... 600/3 |
| 6,589,502 B1 | 7/2003 | Coniglione et al. ........ 424/1.25 |
| 6,608,277 B2 | 8/2003 | Spooner et al. ........ 219/121.63 |
| 6,666,811 B1 | 12/2003 | Good ............................. 600/8 |
| 6,679,824 B1 | 1/2004 | Reed et al. ...................... 600/7 |
| 6,689,043 B1 | 2/2004 | McIntire et al. ................ 600/1 |
| 6,730,013 B1 | 5/2004 | Shank et al. .................... 600/7 |
| 6,749,554 B1 | 6/2004 | Snow et al. ..................... 600/3 |
| 6,821,242 B1 | 11/2004 | Waksman et al. ............... 600/3 |
| 7,316,644 B2 * | 1/2008 | Bray ............................. 600/8 |
| 2002/0022781 A1 | 2/2002 | McIntire et al. ............. 600/458 |
| 2002/0162828 A1 | 11/2002 | Spooner et al. ........ 219/121.63 |
| 2003/0088146 A1 | 5/2003 | Slater et al. .................... 600/8 |
| 2003/0092959 A1 | 5/2003 | Slater et al. .................... 600/8 |
| 2003/0229259 A1 | 12/2003 | Waksman et al. ............... 600/3 |
| 2004/0076579 A1 | 4/2004 | Coniglione et al. ........ 424/1.11 |
| 2004/0097779 A1 | 5/2004 | McIntire et al. ................ 600/1 |
| 2004/0192999 A1 | 9/2004 | Waksman et al. ............... 600/4 |
| 2004/0236169 A1 | 11/2004 | Slater et al. .................... 600/8 |
| 2004/0242953 A1 | 12/2004 | Good ............................. 600/7 |
| 2006/0018813 A1 | 1/2006 | Bray ........................... 423/11 |
| 2006/0024223 A1 | 2/2006 | Bray et al. ...................... 423/1 |
| 2006/0051269 A1 | 3/2006 | Bray et al. ................... 423/158 |
| 2006/0167332 A1 | 7/2006 | Bray ............................. 600/3 |

FOREIGN PATENT DOCUMENTS

| | | |
|---|---|---|
| JP | 01-254900 | 10/1989 |
| WO | WO 00/51136 | 8/2000 |
| WO | WO 01/80251 | 10/2001 |
| WO | WO 2004/053892 | 6/2004 |

OTHER PUBLICATIONS

"Radiation protection—Sealed radioactive sources—General requirements and classification," International Standard ISO 2919, Second Edition, Feb. 15, 1992.

(Continued)

Primary Examiner—Steven Bos
(74) Attorney, Agent, or Firm—Seed IP Law Group PLLC

(57) ABSTRACT

The present invention provides a method for improving the recovery of cesium-131 (Cs-131) from barium (Ba) carbonate. Uses of the Cs-131 purified by the method include cancer research and treatment, such as for the use in brachytherapy. Cesium-131 is particularly useful in the treatment of faster growing tumors.

21 Claims, No Drawings

OTHER PUBLICATIONS

"Radiation protection—Sealed radioactive sources—Leakage test methods," International Standard ISO 9978, First Edition, Feb. 15, 1992.

3M Empore™ Rad Disks Product Listing, 1998. Available at http://www.mmm.com/empore, downloaded Mar. 11, 2004.

Armpilia, C.I. et al., "The Determination of Radiobiologically Optimized Half-lives for Radionuclides Used in Permanent Brachytherapy Implants," *Int. J. Radiation Oncology Biol. Phys.* 55(2): 378-385, 2003.

Balmer, M.L. et al., "New Silicotitanate Waste Forms: Development and Characterization," Interfacial and Processing Sciences Annual Report 1999. Available at http://www.pni.gov/microcats/aboutus/publications/microsystems/annual_report1999. Downloaded Sep. 19, 2004.

Cary, A., "PNNL gel may change drug obstacles," *Tri-City Herald*, Mar. 30, 2001. Available at http://www.tri-cityherald.com. Downloaded Oct. 8, 2004.

Harper, P.V. et al., "Isotopes Decaying by Electron Capture: A New Modality in Brachytherapy," in *Proceedings of the International Conference on the Peaceful Uses of Atomic Energy*, Geneva Switzerland, 1958, pp. 417-422.

Heintz, B.H. et al., "Comparison of I-125 sources used for permanent interstitial implants," *Med. Phys.* 28(4): 671-682, Apr. 2001.

Henschke, U.K. et al., "Cesium-131 Seeds for Permanent Implants," *Radiology* 85(6): 1117-1119, Dec. 1965.

Hobbs, D.T., "Strategic Design and Optimization of Inorganic Sorbents for Cesium, Strontium, and Actinides," Westinghouse Savannah River Company Report WSRC-RP-2002-00337. Available at http://www.osti.gov/bridge. Downloaded Oct. 5, 2005.

Hodgman, C.D. (ed.), "*Handbook of Chemistry and Physics, 31st edition*," Chemical Rubber Publishing Co., Cleveland, OH, pp. 408-409, 1949.

Hodgman, C.D. (ed.), "*Handbook of Chemistry and Physics, 31st edition*," Chemical Rubber Publishing Co., Cleveland, OH, pp. 524-525, 1949.

Korb, L.J. et al., "Modern Brachytherapy for Localized Prostate Cancers: The Northwest Hospital (Seattle) Experience," *Review in Urology* 3(1): 51-60, Winter 2001.

Kraus and Nelson, "Anion Exchange Studies of the Fission Products," in *Proc. Int. Conf. Peaceful Uses of Atomic Energy*, vol. 7, Geneve, 1955, pp. 113-125.

Kurath, D.E. et al., "Ion Exchange Removal of Cesium from Simulated and Actual Hanford Tanks 241-SY-101 and 241-SY-103," in *Proceedings of the International Topical Meeting on Nuclear and Hazardous Waste Management Spectrum '96*, Aug. 18-23, 1996, Seattle, Washington, American Nuclear Society, La Grange Park, IL, 1996, pp. 222-228.

Malinin, A.B. et al., "Production of $^{131}$Cs Without a Carrier and Estimation of the Cross Section of the Reaction $^{131}$Cs (n,γ) $^{132}$Cs on Thermal Neutrons," *Soviet Radiochemistry* 14(6): 896-899, Nov.-Dec. 1972.

Naumann, R.A. et al., "Preparation of Radioactive Targets for Charged-Particle Nuclear Spectroscopy at the CERN-ISOLDE Project," *Nuclear Instruments and Methods in Physics Research B26*: 59-64, 1987.

pSiVida Company, BioSilicon internet web pages. Available at http://www.psivida.com.au/text. Downloaded Nov. 3, 2004.

R. Braun et al., "Crystalline Silicotitanates—Novel Commercial Cesium Ion Exchangers," UOP, pp. 1-12, pre-Nov. 2003.

Smith, L.L. et al., "Application of Empore™ Strontium Rad Disks to the Analysis of Radiostrontium in Environmental Water Samples," *Radiochemica Acts* 73:165-170, 1996.

Wike, J.S. et al., "Chemistry for Commercial Scale Production of Yttrium-90 for Medical Research," *International Journal of Radiation Applications and Instrumentation Part A*, 41(9): 861-865, 1990.

Willard and Goodspeed, "Separation of Strontium, Barium, and Lead from Calcium and Other Metals," *Industrial and Engineering Chemistry* 8(6):414-418, 1936.

* cited by examiner

METHOD FOR IMPROVING THE RECOVERY OF CESIUM-131 FROM BARIUM CARBONATE

CROSS REFERENCE TO RELATED APPLICATION

This application claims the benefit under 35 U.S.C. § 119(e) of U.S. Provisional Patent Application No. 60/777,488 filed Feb. 28, 2006, where this provisional application is incorporated herein by reference in its entirety.

BACKGROUND OF THE INVENTION

1. Field of the Invention

The present invention relates generally to a method for improving the recovery of cesium-131 (Cs-131) from barium (Ba). Uses of the Cs-131 purified by the method include cancer research and treatment, such as for use in brachytherapy implant seeds independent of method of fabrication.

2. Description of the Related Art

Radiation therapy (radiotherapy) refers to the treatment of diseases, including primarily the treatment of tumors such as cancer, with radiation. Radiotherapy is used to destroy malignant or unwanted tissue without causing excessive damage to the nearby healthy tissues.

Ionizing radiation can be used to selectively destroy cancerous cells contained within healthy tissue. Malignant cells are normally more sensitive to radiation than healthy cells. Therefore, by applying radiation of the correct amount over the ideal time period, it is possible to destroy essentially all of the undesired cancer cells while saving or minimizing damage to the healthy tissue. For many decades, localized cancer has often been cured by the application of a carefully determined quantity of ionizing radiation during an appropriate period of time. Various methods have been developed for irradiating cancerous tissue while minimizing damage to the nearby healthy tissue. Such methods include the use of high-energy radiation beams from linear accelerators and other devices designed for use in external beam radiotherapy.

Another method of radiotherapy comprises brachytherapy. Here, radioactive substances in the form of seeds, needles, wires or catheters are implanted permanently or temporarily directed into/near the cancerous tumor. Historically, radioactive materials used have included radon, radium and iridium-192. More recently, the radioactive isotopes Cs-131, iodine-125 (I-215), and palladium-103 (Pd-103) have been used. Examples are described in U.S. Pat. Nos. 3,351,049; 4,323,055; and 4,784,116.

During the last 30 years, numerous articles have been published on the use of I-125 and Pd-103 in treating prostate cancer. Despite the demonstrated success in certain regards of I-125 and Pd-103, there are certain disadvantages and limitations in their use. While the total dose can be controlled by the quantity and spacing of the seeds, the dose rate is set by the half-life of the radioisotope (60 days for I-125 and 17 days for Pd-103). For use in faster growing tumors, the radiation should be delivered to the cancerous cells at a faster rate, while simultaneously preserving all of the advantages of using a soft x-ray emitting radioisotope. Such cancers are often found in the brain, lung, pancreas, prostate and other tissues.

Cesium-131 (Cs-131) is a radionuclide product that is ideally suited for use in brachytherapy (cancer treatment using interstitial implants, i.e., "radioactive seeds"). The short half-life of Cs-131 makes the seeds effective against faster growing tumors such as those found in the brain, lung, and other sites. While prostate cancer is generally considered slower growing, certain prostate cancers are more aggressive and more appropriately treated using an isotope with a shorter half-life such as Cs-131. The shorter half-life of Cs-131 is equally effective against the slower growing tumors and thus is applicable for treatment where the aggressiveness of the tumor is not well known in advance (C. I. Armpilia et al., *Int. J. Radiat. Oncol. Biol. Phys.* 55:378-385 (2003)).

Cesium-131 is produced by radioactive decay from neutron irradiated naturally occurring Ba-130 (natural Ba comprises about 0.1% Ba-130) or from enriched barium containing additional Ba-130, which captures a neutron, becoming barium-131 (Ba-131). The source of the neutrons can be a nuclear reactor or other neutron generating devices (e.g., neutron generators). Barium-131 then decays with an 11.7-day half-life to cesium-131, which subsequently decays with a 9.7-day half-life to stable xenon-130. Thus, with the decay of Ba-131 comes the buildup of Cs-131. To separate the Cs-131, the barium target is "milked" multiple times over selected intervals such as 7 to 14 days, as Ba-131 decays to Cs-131. With each "milking," the Curies of Cs-131 present and the gram ratio of Cs to total Ba decreases (less Cs-131 per gram of Ba) until it is not economically of value to continue to "milk the cow" (e.g., after approximately 40 days). The barium "target" can then be returned to the reactor for further irradiation (if sufficient Ba-130 is present) or discarded.

In order for the Cs-131 product to be useful, the Cs-131 must be exceptionally pure, free from other metal (e.g., barium, calcium, iron, cobalt, etc.) and radioactive ions including Ba-131. A typical radionuclide purity acceptance criteria for Cs-131 is >99.9% Cs-131 and <0.01% Ba-131.

The objective in producing highly purified Cs-131 from irradiated barium is to completely separate less than $7 \times 10^{-7}$ grams (0.7 μg) of Cs from each gram (1,000,000 μg) of barium "target." A typical target size may range from several grams to several kilograms of Ba, depending on whether enriched Ba-130 or natural target is used in irradiation (natural Ba comprises about 0.1% Ba-130). Typically, irradiated Ba targets comprise various Ba salts. Most often barium carbonate is used. Because Cs-131 is formed in the $BaCO_3$ crystal structure during decay of Ba-131, it is assumed that the Ba "target" must first be dissolved to release the very soluble Cs ion.

As noted above, Cs is a very small fraction (about less than 0.0001%) of the irradiated barium target, and thus it is beneficial to be able to recover the Cs in good yield. This is particularly true where processes for production of Cs-131 from Ba are scaled-up. Current approaches typically involve dissolution of the Ba targets in acid to release $Cs^{+1}$ ions. Commonly acetic acid is used for dissolution. The dissolution step is followed by precipitation of Ba in the form of a compound with limited solubility in water, while $Cs^{+1}$ ions remain in solution and thus separated from Ba. Commonly, Ba is precipitated as carbonate using ammonium carbonate $(NH_4)_2CO_3$ solution as the precipitating reagent. While other carbonates can be used (e.g., Li, Na, etc.), the advantage of using precipitating reagents based on ammonium salts is the ease of separating Cs from ammonium ions.

Following precipitation, the liquid containing Cs is separated from the barium precipitate by common methods (such as filtering or centrifuging) followed by evaporation to dryness of the acetate or other organic acid salts formed during Cs-131 separation from Ba carbonate. This is then followed by use of dilute acetic acid for dissolution of Cs salts. A disadvantage is that currently the recoveries using such procedures are generally on the order of only 30%-50%. The remaining balance of Cs-131 is associated with an organic, carbonaceous residue formed during evaporation of the filtrate solution containing Cs, ammonium acetate and ammonium carbonate salts. One further disadvantage of the current approaches for using ammonium carbonate solution as a precipitant is the limited solubility of the ammonium carbonate reagent in water (less than 3 moles/L). Limited solubility of the precipitating reagent results in an undesirable increase in the total volume of solution remaining after the Ba precipitation step. Increased solution volume requires larger scale equipment and lengthens the evaporation process. These are particularly problematic for implementation of large scale (>100 g) target processing. In this manner, the disadvantages to the current approach of using ammonium carbonate as the precipitating reagent are associated with the formation of a carbonaceous residue during the evaporation of ammonium acetate and the limited solubility of this reagent in water.

Due to the need for better Cs-131 recoveries and the deficiencies in the current approaches in the art, there is a need for improved methods. The present invention fulfills this need and further provides other related advantages.

BRIEF SUMMARY OF THE INVENTION

Briefly stated, the present invention discloses a method for improving the recovery of Cs-131 from Ba. In an embodiment, the method comprises the steps of: (a) dissolving neutron-irradiated barium comprising barium carbonate and Cs-131, in a first solution comprising an acid which reacts with the barium to form a soluble barium salt, whereby the barium and Cs-131 are dissolved in the first solution; (b) precipitating the barium as a carbonate solid, whereby the Cs-131 remains dissolved in the first solution; (c) separating the solids from the solution containing the Cs-131; (d) evaporating the solution containing the Cs-131 to incipient dryness to leave a residue; (e) subjecting the residue to oxidative treatment to yield a digested residue; (f) contacting the digested residue with a solution whereby the Cs-131 goes into the solution; and (g) separating the digested residue from the solution, thereby purifying the Cs-131.

In an embodiment of the method, step (b) comprises adding the first solution to a second solution comprising ammonium carbonate, under conditions of rate of addition and mixing sufficient to precipitate the barium as a solid, whereby the Cs-131 remains dissolved in the combined solution of the first and second solutions.

In an embodiment of the method, step (b) comprises adding a second solution comprising aqueous ammonia to the first solution and adding $CO_2$ as a gas or solid to the combined solution of the first and second solutions under conditions of rate of addition and mixing sufficient to precipitate the barium as a solid, whereby the Cs-131 remains dissolved in the combined solution of the first and second solutions.

In an embodiment of the method, step (b) comprises adding ammonia gas and $CO_2$ as a gas or solid to the first solution under conditions of rate of addition and mixing sufficient to precipitate the barium as a solid, whereby the Cs-131 remains dissolved in the first solution.

In an embodiment of the method, after step (c), steam is delivered to the solution under conditions sufficient to distill volatile ammonium salts from the solution.

In an embodiment of the method, the separated solids of step (c) are subjected to the steps of: (i) storing the solids to allow additional Cs-131 to form from decay of Ba-131; and (ii) repeating steps (a)-(g) as set forth above.

In an embodiment of the method, the temperature during the end of evaporation step (d) is less than 250° C.

In an embodiment of the method, the oxidative treatment of step (e) comprises thermal ashing, followed by digestion of the residue using an oxidizing chemical agent to yield a digested residue.

In an embodiment of the method, thermal ashing comprises thermal treatment in the presence of an oxidizing environment at temperatures between 250° C.-1000° C.

In an embodiment of the method, the oxidizing chemical agent is selected from one or more of hot concentrated nitric acid, hot concentrated sulfuric acid, a peroxidisulfate salt, a cerium (IV) compound and a Cr (VI) compound.

In an embodiment of the method, the acid of step (a) is acetic acid.

In an embodiment of the method, the acid of step (a) is nitric acid.

In an embodiment of the method, the solution of step (f) comprises water, acid or base.

In an embodiment of the method, steps (a) through (g) are repeated on one or more additional neutron-irradiated barium targets and the purified Cs-131 of step (g) and repeated step (g) are combined.

In an embodiment of the method, prior to step (c), the first solution containing the solid of step (b) is subjected to heat with stirring for a time and temperature sufficient to digest the solid, cooled to room temperature to permit a solid to precipitate, and subjected to step (c).

In an embodiment of the method, prior to step (d), the solids separated in step (c) are washed with water and the wash solution combined with the solution of step (c) containing the Cs-131.

The present invention provides purified Cs-131 comprising Cs-131 prepared by a method of the present invention.

The present invention provides a radioactive brachytherapy implant substance comprising a brachytherapy implant substance containing Cs-131 prepared by a method of the present invention.

These and other aspects of the present invention will become apparent upon reference to the following detailed description.

DETAILED DESCRIPTION OF THE INVENTION

The present invention provides a method for purifying Cs-131 that improves the recovery of Cs-131 from barium carbonate. The barium carbonate may be irradiated target material or a precipitated form of barium. The method is efficient and economical for large scale commercial production of Cs-131. Cesium-131 recoveries using the present invention are on the order of at least 70%-90% (typically in excess of 85%).

Neutron irradiation of a barium target to produce Ba-131, which then decays to Cs-131, is well known to one in the art (e.g., Harper, P. V. et al., *Proceedings of the International Conference on the Peaceful Uses of Atomic Energy, 2nd,* Geneva, Switzerland, 1958, pp. 417-422). The irradiated Ba target comprising barium carbonate and Cs-131 is then dissolved in a solution comprising an acid in order to dissolve the barium and Cs-131. The acid possesses the ability to react with the barium to form a soluble barium salt. Such acids are well known to one in the art, and include, for example, acetic acid, formic acid and nitric acid. It may be desirable that the acid additionally forms readily decomposable ammonium salts. The above listed acids possess this property as well.

The barium in the solution (with dissolved barium and Cs-131) is precipitated as a carbonate solid, and the Cs-131 remains dissolved in the solution. In one embodiment, the solution with dissolved barium and Cs-131 is then added to a second solution comprising ammonium carbonate under conditions sufficient to precipitate the barium as a solid (e.g., U.S. Application Publication No. US-2006-0024223-A1). The Cs-131 remains dissolved in the combined solution. In another embodiment, a second solution comprising an aqueous solution of ammonia is added to the first solution and $CO_2$ as a gas or solid is delivered through the mixed solution under conditions sufficient to precipitate the barium as barium carbonate solid, while the Cs-131 remains dissolved. In yet another embodiment of this invention, ammonia gas and $CO_2$ as a gas or solid are delivered to the solution such that Ba is precipitated as carbonate solid, while Cs-131 remains in solution. The $CO_2$ may be added to the solution after the ammonia gas is delivered. Alternatively, the ammonia gas and the $CO_2$ are added simultaneously to the solution.

The solids produced by any of the embodiments are separated from the solution containing the Cs-131 by techniques well known to one in the art (e.g., U.S. Application Publication No. US-2006-0024223-A1), including by filtration, centrifuging or decanting. Prior to separating the solids from the solution, the solution may be subjected to heat with stirring for a time and temperature sufficient to digest the solids, cooled to room temperature to permit solids to precipitate, and then subjected to the separation step. After the separation step, the solids may be washed one or more times with water and the wash solutions combined with the solution containing the Cs-131 from the separation step. The solids containing the barium are typically stored to allow additional Cs-131 to form from further decay of Ba-131. The solids may then be processed again, as just described for the initial processing of the irradiated Ba target.

The Cs-131 remains dissolved in the solution from which the barium is precipitated and removed. As described above, evaporation has been used to remove substances in the solution (such as ammonium acetate salts) that are capable of volatilization. The evaporation must be carried out at sufficiently high temperature to enable rapid volatilization. It may be desirable to deliver steam to the solution prior to or during (e.g., at the beginning of) the evaporation step for a period of time so that volatile ammonium salts such as ammonium acetate and organic impurities are volatilized prior to taking the solution to incipient dryness, thus minimizing the amount of carbonaceous (organic) material formed. The evaporation step results in formation of an organic carbonaceous residue. The organic residue material was found to hold a significant amount of Cs-131 which could not be released when the organic residue was treated with mineral acids, acetic acid, ammonia or ammonium acetate. The present invention addresses the problem of poor recovery of Cs-131 from the residue obtained by evaporation of the acetate or other organic acid salts formed during Cs-131 separation from barium carbonate.

In the present invention, oxidative treatment of the organic residue material using thermal ashing or chemical ashing or both, results in conversion of the organic residue to carbon-like material in a form that allows recovery of the Cs-131 by washing with water or dilute mineral or organic acids. By use of an oxidative treatment step, chemical recovery of the Cs-131 is 70%-90%. Thus, by converting the organic residue to a form from which Cs-131 can be effectively recovered by leaching or washing with an aqueous solution, as much as about a 50% increase in the recovery of Cs-131 may be achieved.

In embodiments of the present invention, the combined solution containing the Cs-131 (from which the solids containing barium have been separated) is processed as follows. The evaporation (with or without prior or simultaneous steam treatment) of the combined solution containing the Cs-131 is carried out to incipient dryness. In an embodiment, the evaporation step is carried out at controlled temperatures to minimize formation of the organic residue. For example, the temperature during the end of the evaporation step is less than 250° C. It is preferred that heating is carried in a manner that precludes condensation of the volatilized solids on the walls of the vessel (i.e., through uniform heating of the evaporation vessel).

In an embodiment, the residue formed after evaporation of volatile salts is thermally treated in an oxidizing environment (such as air) at temperatures between about 250° C.-1000° C. to convert organic material to ash or carbon. For example, the temperature for thermal oxidative treatment is between 400° C. and 500° C. The time period for oxidative treatment is typically between about 1 and 24 hours. Alternatively, or in combination with thermal oxidation, the digestion of the organic residue may be carried out by using an oxidizing chemical agent or combinations of such agents. Examples of chemical oxidants that may be used alone or in combination include hot concentrated nitric acid, hot concentrated sulfuric acid, peroxidisulfate salts, cerium (IV) compounds and Cr (VI) compounds. A specific example includes addition of 10 mL of 96% sulfuric acid to the residue and heating the vessel to 300° C. until all the sulfuric acid is volatilized. Based on the disclosure provided herein, it will be evident to one in the art that other chemical oxidants and combinations of oxidants are possible. The chemical digestion process may be carried out at elevated temperature, for example, using resistive or microwave heating in open or closed digestion vessels.

Following the oxidative treatment, the Cs-131 may be recovered in a variety of ways. For example, any remaining organic residue may be contacted with an aqueous solution. Aqueous solutions include water, acids or bases (e.g., dilute acids or dilute bases). Cesium-131 in the residue will go into the aqueous solution. The residue is separated from the aqueous solution, thereby purifying the Cs-131. The separation may be accomplished by a variety of means. For example, the residue may be removed from the solution by filtration.

The following is an example of chemical oxidative treatment. In this example, the oxidative treatment is performed using a combination of sulfuric acid and nitric acid. Neutron-irradiated Ba carbonate (1800 g) is processed using acetic acid dissolution. The Ba is precipitated using ammonium carbonate. The solution is separated from the precipitate, and is evaporated to incipient dryness to leave an organic residue. The organic residue is treated with sulfuric acid (1-5 ml) and nitric acid (5-10 ml). Digestion is carried out under conditions that minimize vapor loss. Following a digestion period of 1 to 3 hours, the solution is taken to incipient dryness until complete evaporation of sulfuric acid is achieved. Alternatively for digestion, sulfuric acid may be added to the organic residue in an amount sufficient to wet the residue, digested for several hours under conditions that minimize vapor loss and then the residue is taken to incipient dryness. Following the oxidative treatment (by either the combination of sulfuric acid and nitric acid, or sulfuric acid alone), the Cs-131 is recovered by washing any remaining residue with water, acids or bases (e.g., dilute acids or dilute bases). The digested residue is separated from the Cs-131 containing solution by filtration. Chemical recoveries of Cs-131 are typically in excess of 85%.

As used herein, the term "separating" two things (e.g., solids and solution, or residue and solution) may refer to the removal of the first from the second, or the second from the first, or the removal of both simultaneously. For example, "separating the Cs-131" may mean removing the Cs-131 from the irradiated barium target, or removing the irradiated barium target from the Cs-131, or removal of both simultaneously. In addition, as used herein, the irradiated barium target may have been partially purified prior to separating the Cs-131.

Procedures for separating Cs-131 from irradiated barium targets are well known in the art (e.g., U.S. Pat. No. 6,066, 302). For example, chemical separation steps can be utilized to isolate Cs-131 from the target material and radioactive impurities that may have been produced in the target material. The solution containing the Cs-131 may also have chemical and radioactive impurities that were present in the irradiated target or that were introduced during processing. Examples of such impurities are cerium (Ce) or chromium (Cr) ions. Separation techniques include precipitation, sorption, extraction, solid phase extraction, ion exchange and combinations thereof. In an embodiment of precipitation, the impurities are precipitated while Cs remains in solution. Examples of precipitates are $Fe(OH)_3$, $BaCO_3$ or $BaSO_4$. In an embodiment of precipitation, the Cs is precipitated while the impurities remain in solution. Examples of precipitating reagents that selectively remove Cs leaving the impurities in solution are ammonium molybdophosphate or cyannoferrates. In an embodiment of extraction, the solution is treated with a solvent which is an extractant with affinities for a broad group of metal ions with the exception of the alkali group elements, including Cs. Thus impurities are solvent extracted while Cs remains in solution. An example is the organiphosphoric liquid cation exchanger extractant di(2-ethylhexyl)orthophosphoric acid (HDEHP). In an embodiment of extraction, Cs is extracted into an organic solvent, while the impurities remain in the aqueous phase. Examples of organic solvents include phenols and crown ethers, such as mono- or bis-crown-6 ethers, and crown ether derivatives of calix[4]-arenes. In embodiments of solid phase extraction, extractants are immobilized onto solid supports and may be deployed as packing in columns. As described above, the extractant may have affinity for Cs (so that the impurities remain in solution) or for impurities (so that the Cs remains in solution). In an embodiment of ion exchange, the ion exchange media (which may be used in a column) selectively retains impurities but not Cs. Examples of suitable ion exchange media include chelating resins with suitable functionality such as iminodiacetate (e.g., Chelex 100 from Sigma Aldrich) or similar media. In an embodiment of ion exchange, both Cs and impurities are retained by the ion exchange media (which may be used in a column); however, impurities are preferentially eluted using a complexant. Examples of suitable complexants include EDTA or oxalates. Examples of cation exchange resins include conventional cation exchange resins with sulfonic acid functionalities.

One or more neutron-irradiated barium targets may be similarly processed (as described in the steps above) and the additional purified Cs-131 may be combined with the purified Cs-131 obtained from initial processing of a more recently irradiated Ba target.

As described above, Cs-131 is useful for example for radiotherapy (such as to treat malignancies). Where it is desired to implant a radioactive substance (e.g., Cs-131) into/near a tumor for therapy (brachytherapy), Cs-131 may be used as part of the fabrication of brachytherapy implant substance (e.g., a seed). A brachytherapy implant substance containing Cs-131 may be incorporated into a device. The use of Cs-131 in brachytherapy implant substances is not dependent on the method of fabrication of the substances. A method of the present invention provides purified Cs-131 for these and other uses.

The following Examples are offered by way of illustration and not by way of limitation.

EXAMPLE

Cs/BA Separation Procedure

Dissolve 1500 g of irradiated $BaCO_3$ in 3.7 liters of water using 20 moles of glacial acetic acid (17.4 M). Perform addition of the acetic acid slowly to minimize foaming. Provide gentle heat and stirring to speed the dissolution process.

Slowly add solution to 7.3 liters of saturated ammonium carbonate solution. Provide stirring to allow barium carbonate precipitate to form.

Heat the precipitate to near boiling temperature for 2 hours with stirring to digest the precipitate.

Cool the mixture to room temperature.

Filter the precipitate and rinse the solids twice with 1 liter of water.

Combine the filtrate and wash solutions (~14.1 liters) and evaporate to incipient dryness.

Digest carbonaceous residue at 500° C. for 2 hours. Allow to cool to ambient temperature.

Add 20 mL of 96% sulfuric acid. Heat to 300° C. until the acid is volatilized and no further evolution of white fumes is evident.

Cool to room temperature.

Add two portions of 50 mL of water, stir and filter the precipitate.

Combine the filtrate and evaporate to dryness in a suitable container. Chemical recovery of Cs-131 is approximately 90%. The Cs-131 product contains no detectable Ba-131.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for purifying Cs-131, comprising the steps of:
   (a) dissolving neutron-irradiated barium comprising barium carbonate and Cs-131, in a first solution comprising an acid which reacts with the barium to form a soluble barium salt, whereby the barium and Cs-131 are dissolved in the first solution;
   (b) precipitating the barium as a carbonate solid, whereby the Cs-131 remains dissolved in the first solution;
   (c) separating the solids from the solution containing the Cs-131;
   (d) evaporating the solution containing the Cs-131 to incipient dryness to leave a residue;
   (e) subjecting the residue to oxidative treatment to yield a digested residue;
   (f) contacting the digested residue with an aqueous solution whereby the Cs-131 goes into the aqueous solution; and
   (g) separating the digested residue from the solution of step (f), thereby purifying the Cs-131.

2. The method according to claim 1 wherein step (b) comprises adding the first solution to a second solution comprising ammonium carbonate, under conditions of rate of addition and mixing sufficient to precipitate the barium as a solid, whereby the Cs-131 remains dissolved in the combined solution of the first and second solutions.

3. The method according to claim 1 wherein step (b) comprises adding a second solution comprising aqueous ammonia to the first solution and adding $CO_2$ as a gas or solid to the combined solution of the first and second solutions under conditions of rate of addition and mixing sufficient to precipitate the barium as a solid, whereby the Cs-131 remains dissolved in the combined solution of the first and second solutions.

4. The method according to claim 1 wherein step (b) comprises adding ammonia gas and $CO_2$ as a gas or solid to the first solution under conditions of rate of addition and mixing sufficient to precipitate the barium as a solid, whereby the Cs-131 remains dissolved in the first solution.

5. The method according to claim 4 wherein the $CO_2$ is added after the ammonia gas.

6. The method according to claim 4 wherein the ammonia gas and the $CO_2$ are added simultaneously.

7. The method according to claim 1 wherein after step (c), steam is delivered to the solution of step (c) under conditions sufficient to distill volatile ammonium salts from the solution.

8. The method according to claim 7 wherein delivering steam to the solution is a separate step introduced between step (c) and step (d).

9. The method according to claim 7 wherein the steam is delivered to the solution beginning at the initiation of step (d).

10. The method according to claim 1 wherein the separated solids of step (c) are subjected to the steps of:
  (i) storing the solids to allow additional Cs-131 to form from decay of Ba-131; and
  (ii) repeating steps (a)-(g) of claim 1.

11. The method according to claim 1 wherein the temperature during the end of evaporation step (d) is less than 250° C.

12. The method according to claim 1 wherein the oxidative treatment of step (e) comprises thermal ashing, followed by digestion of the residue using an oxidizing chemical agent to yield a digested residue.

13. The method according to claim 12 wherein thermal ashing comprises thermal treatment in the presence of an oxidizing environment at temperatures between 250° C.-1000° C.

14. The method according to claim 13 wherein the temperature is between 400° C. and 500° C.

15. The method according to claim 12 wherein the oxidizing chemical agent is selected from one or more of hot concentrated nitric acid, hot concentrated sulfuric acid, a peroxidisulfate salt, a cerium (IV) compound and a Cr (VI) compound.

16. The method according to claim 1 wherein the acid of step (a) is acetic acid.

17. The method according to claim 1 wherein the acid of step (a) is nitric acid.

18. The method according to claim 1 wherein the solution of step (f) comprises water, acid or base.

19. The method according to claim 1 wherein steps (a) through (g) are repeated on one or more additional neutron-irradiated barium targets and the purified Cs-131 of step (g) and repeated step (g) are combined.

20. The method according to claim 1 wherein prior to step (c), the first solution containing the solid of step (b) is subjected to heat with stirring for a time and temperature sufficient to digest the solid, cooled to room temperature to permit a solid to precipitate, and subjected to step (c).

21. The method according to claim 1 or claim 20 wherein prior to step (d), the solids separated in step (c) are washed with water and the wash solution combined with the solution of step (c) containing the Cs-131.

* * * * *